(12) United States Patent
Sahin et al.

(10) Patent No.: US 10,125,453 B2
(45) Date of Patent: Nov. 13, 2018

(54) ANTIMICROBIAL TEXTILE PRODUCTS AND METHOD OF OBTAINING THEREOF

(71) Applicant: YEDITEPE ÜNIVERSITESI, Istanbul (TR)

(72) Inventors: Fikrettin Sahin, Istanbul (TR); Selami Demirci, Istanbul (TR); Okan Demir, Istanbul (TR); Zeynep Ustaoglu, Istanbul (TR)

(73) Assignee: YEDITEPE ÜNIVERSITESI, Istanbul (TR)

( * ) Notice: Subject to any disclaimer, the term of this patent is extended or adjusted under 35 U.S.C. 154(b) by 324 days.

(21) Appl. No.: 14/915,257

(22) PCT Filed: Aug. 14, 2014

(86) PCT No.: PCT/TR2014/000315
§ 371 (c)(1),
(2) Date: Feb. 29, 2016

(87) PCT Pub. No.: WO2015/038080
PCT Pub. Date: Mar. 19, 2015

(65) Prior Publication Data
US 2016/0215442 A1 Jul. 28, 2016

(30) Foreign Application Priority Data

Sep. 12, 2013 (TR) .............. a 2013 10764

(51) Int. Cl.
| | | |
|---|---|---|
| *D06M 11/82* | (2006.01) | |
| *D06M 13/165* | (2006.01) | |
| *A01N 31/16* | (2006.01) | |
| *A01N 47/44* | (2006.01) | |
| *A01N 59/14* | (2006.01) | |
| *D06M 13/156* | (2006.01) | |
| *D06M 13/175* | (2006.01) | |
| *D06M 13/432* | (2006.01) | |
| *D06M 15/11* | (2006.01) | |
| *D06M 16/00* | (2006.01) | |
| *A01N 43/16* | (2006.01) | |

(52) U.S. Cl.
CPC ........... *D06M 13/165* (2013.01); *A01N 31/16* (2013.01); *A01N 43/16* (2013.01); *A01N 47/44* (2013.01); *A01N 59/14* (2013.01); *D06M 11/82* (2013.01); *D06M 13/156* (2013.01); *D06M 13/175* (2013.01); *D06M 13/432* (2013.01); *D06M 15/11* (2013.01); *D06M 16/00* (2013.01); *A61L 2300/202* (2013.01); *A61L 2300/404* (2013.01); *A61L 2300/44* (2013.01); *A61L 2300/45* (2013.01)

(58) Field of Classification Search
CPC .. D06M 11/82; D06M 13/156; D06M 13/165; D06M 13/175; D06M 13/432; D06M 16/00; A01N 31/16; A01N 47/44; A01N 59/14; A61L 12/141; A61L 2300/202; A61L 2300/404
See application file for complete search history.

(56) References Cited

U.S. PATENT DOCUMENTS

| | | | |
|---|---|---|---|
| 6,224,579 B1 * | 5/2001 | Modak | A01N 59/16 424/422 |
| 2008/0033329 A1 | 2/2008 | Downs et al. | |
| 2013/0152277 A1 | 6/2013 | Rakitin | |
| 2016/0032523 A1 * | 2/2016 | Liu | D06P 5/30 347/21 |

FOREIGN PATENT DOCUMENTS

| | | | | |
|---|---|---|---|---|
| WO | WO-2012034032 A2 * | 3/2012 | ........... | A61L 21/186 |
| WO | WO2012034032 A2 | 3/2012 | | |
| WO | WO-2013072883 A1 * | 5/2013 | ............ | D06M 11/82 |
| WO | WO2013072883 A1 | 5/2013 | | |

OTHER PUBLICATIONS

Wenzel, R. P. and Edmond. M. B. (2013). "Listening to SARS: lessons fer infection control." Annals of internal medicine 139(7): 592-593
Yamaguchie, E., Valena, F., Smith, S. M., Simmons, A. and Eng. R. H. (1994). "Colonization pattern of vancomycin-resistant Enterococcus faecium." American journal of infection control 22(4): 202-206.
Fijan, S., Sostar-Turk, S. and Cencic, A. (2005). "Implementing hygiene monitoring systems in hospital laundries in order to reduce microbial contamination of hospital textiles," The Journal of hospital infection 61(1): 30.
Larson, E. L. (1999). "Home hygiene: a reemerging issue for the new millennium." American journal of infection control 27(6): S1-S3.
Lalitha, M. (2005). "Manual an antimicrobial susceptibiiity testing."
Nguyen Q. V. (2006). "Hospital-acquired infections." eMedicine, Aug. 21.

* cited by examiner

*Primary Examiner* — Arti Singh-Pandey
(74) *Attorney, Agent, or Firm* — Gokalp Bayramoglu

(57) ABSTRACT

The present invention relates to a method of obtaining antifungal, anticandidal and antibacterial textile products. The objective of the present invention is to obtain an antimicrobial product, which enables to reduce the infectious diseases that are transmitted or spread by textile products, reduces extra cost and energy spent for ensuring hygiene, and increases hygienity of disposable textile products. A solution of triclosan, chlorhexidine and disodium octaborate pentahydrate is used in the method of the present invention. The said solution enables the hydrophobic textile products to be transformed into hydrophilic products and thereby enables the antimicrobial agents in the solution to be coded into the textile products.

11 Claims, No Drawings

ANTIMICROBIAL TEXTILE PRODUCTS AND METHOD OF OBTAINING THEREOF

FIELD OF THE INVENTION

The present invention relates to a method of obtaining antifungal, anticandidal, and antibacterial textile products.

BACKGROUND OF THE INVENTION

Pathogenic, opportunistic, or beneficial microorganisms proliferate by using the inorganic and organic nutrients on the surfaces and in moisture to form colonies in the region where they are located. Surface contamination and pathogens remaining on the surface for a long period of time increase the risk of environmental and hospital-acquired infections. It has been stated in the literature that decreasing environmental pathogenic load is an important step in hospital-acquired disease reduction (Wenzel and Edmond, 2003). A great majority of the pathogens can live on surfaces for a long period of time and cause serious diseases if the disease becomes widespread upon transmission via direct contact and inhalation. It was shown that vancomycin-resistant *Enterococcus* species, which is one of the most important of these pathogens, was isolated from door knobs, bed sheets, bed rails, tables, walls, floors, and other surfaces in hospitals (Yamaguchie et al., 1994). Since surfaces in hospitals are suitable for microbial growth, a few hours after admission to the hospital, the microorganisms on surfaces in the hospital can start to grow and proliferate on the skin, respiratory tract, urinary tract, and perineal area of the patient (Nguyen, 2006). For these reasons, making all the surfaces in intensive care units, wherein particularly patients with suppressed or weak immune system are treated, emergency response centers and other health care units, nurseries, kindergartens, public transportation, and other public areas, antimicrobial has become an important area, which is under great interests among the scientists.

The primary surfaces desired to be made antimicrobial are the textile products which are continuously and directly in contact with human skin. Since textile products are rich in nutrients and many textile products can retain moisture in the air, they provide all necessary conditions of growth for microorganisms. In environments such as hospitals, where sterilization is extremely important, contamination risk can be reduced by washing the textile products frequently or destroying disposable products after use. Since the textile products used in health care units may accommodate many pathogens thereon, in addition to removing stains from these products, the microbial load thereon should also be removed (Fijan et al. 2005). Although there are no scientific studies proving the direct relationship between the microbial loads on textiles and infectious diseases, it was stated that some microbial species can survive on textiles even after washing (Larson, 1999). Furthermore, disposable products, even though packaged under sterile conditions, provide a suitable environment for microorganism colonization as soon as they are taken out of their packages. Since washing and use of disposable products cannot completely eliminate the microbial load in such places, antimicrobial textile products are needed which will decrease infectious risk and cross contamination and will not allow any microbial load thereon.

Some products, such as nonwovens, which constitute a large part of the textile products, are naturally hydrophobic. However, in various products developed by using these fabrics, particularly in hygienic products (such as hygienic pads and diapers), water absorption is a required property. Thus, these type of products, at least certain parts thereof, should be made hydrophilic. In addition, hydrophilic textile products are also required during the coating process performed with water soluble dyes. Thus, prior to the application of water soluble dyes, a hydrophobic textile product should be made hydrophilic. Apart from these, in order to develop antimicrobial textile products, the surface should be made hydrophilic and the active substance should be allowed to be coded into the textile.

United States patent document No. US2013152277 discloses a garment which is an antimicrobial textile product.

International patent document No. WO2013072883 discloses an antifungal, anticandidal and antibacterial textile product.

SUMMARY OF THE INVENTION

An objective of the present invention is to obtain disposable and reusable antimicrobial textile products.

Another objective of the present invention is to obtain antimicrobial textile products which enable the reduction of infectious diseases that are transmitted or spread via textile products.

A further objective of the present invention is to obtain antimicrobial textile products which reduce extra costs and energy spent to ensure that the textile product is hygienic.

Another objective of the present invention is to obtain a solution which enables the transformation of hydrophobic textile products into hydrophilic textile products.

DETAILED DESCRIPTION OF THE INVENTION

The steps of the method performed for obtaining the antimicrobial textile products of the present invention are as follows:

Experimental Studies

The study conducted comprises the steps of dissolving triclosan in alkyl polyglycoside (glucopon) and obtaining a homogenous mixture, adding chlorhexidine solution to the obtained solution, adding disodium octaborate pentahydrate solution to the triclosan+chlorhexidine solution, and upon achieving a homogenous mixture, obtaining antimicrobial impregnation solution, loading the impregnation solution on the textile products thereby making the products antimicrobial, passing the textile product though the rollers thereby recovering the excess solution, drying the textile products, which are loaded with impregnation solution, by passing them through the ovens, after drying, obtaining the final antimicrobial textile product.

When realizing the invention, powder triclosan was dissolved in 10% alkyl polyglycoside (glucopan) by gently mixing at a concentration of 0.001-0.1% at 45° C. and a homogenous mixture was obtained. 20% chlorhexidine solution was added to the prepared solution at a concentration of 0.05-3%. Finally, homogenous impregnation solution was obtained by mixing high purity and mineralized disodium octaborate pentahydrate solution into the prepared solution at a concentration of 0.001-0.1%.

The final mixture that was obtained was loaded on the textile products by the help of an industrial device thereby making them antimicrobial. After the textile products were passed through the impregnation solution in the impregnating tank, they were passed through the industrial rollers thereby recovering the excess solution. The textile products, which were loaded with the impregnation solution, were dried by being passed through the oven at 60° C. temperature at a speed of 12 meters/minute. Antimicrobial properties of the obtained textile products against bacteria, yeasts and fungi were evaluated by using standard disc diffusion method.

Characterization Studies

Disc Diffusion Method

Antimicrobial properties of the textile products loaded with impregnation solution were examined by using standard NCCLS disc diffusion method (Lalitha, 2005). Briefly, the 100 μl solution including $10^8$ cfu/ml bacteria, $10^6$ cfu/ml yeast, and $10^4$ spor/ml fungus was prepared with new cultures and inoculated with spreading method on Trypticase soy agar (TSA), Sabouraud Dextrose Agar (SDA), and Potato Dextrose Agar (PDA), respectively. The sections of approximately 1×1 cm, which were cut out from the textile products loaded with the impregnation solution comprising the stated concentrations of triclosan, chlorhexidine and disodium octaborate pentahydrate, were placed on inoculated petri dishes. Empty textile products which were not loaded with impregnation solution were used as negative control. As positive control, Ofloxacin (5 μg/disc) was used for bacteria and Nystatin (100 u/disc) was used for yeasts and fungi. The petri dishes, which were inoculated and on which textile products were placed, were kept at 36±1° C. for bacteria for 24 hours and 48 hours for yeasts and at 25±1° C. for fungi for 72 hours. Antimicrobial activity against microorganisms tested in standard disc diffusion method was assessed by measuring the inhibition zone. All tests were repeated at least twice. Antimicrobial activity results of the tested textile products are summarized in Table 1.

Experiment Results

Antimicrobial Test Results

While inhibition zones against the tested microorganisms were observed around the sections, which were cut out from the textile products loaded with the impregnation solution comprising triclosan, chlorhexidine and disodium octaborate pentahydrate prepared by the method applied for obtaining the inventive antimicrobial textile product; inhibition zones were not detected around the sections of the textile product in control group (Table 1). Antibacterial, anticandidal, and antifungal properties were rendered to the textile products by using an impregnation solution prepared with optimized concentrations of active molecules.

TABLE 1

In vitro antimicrobial test results against the selected bacteria, fungi and yeast isolates/strains of textile products loaded with antimicrobial impregnation solution.

|  | Textile Loaded with Impregnation Solution | Standard Textile | Positive Control |
|---|---|---|---|
| BACTERIA |  |  | Ofloxacin (10 μg/disc) |
| *Escherichia coli* | + | − | + |
| *Staphylococcus aureus* | + | − | + |
| MRSA | + | − | + |
| *Pseudomonas aeruginosa* | + | − | + |
| YEASTS |  |  | Nystatin (100 u/disc) |
| *Candida* spp. | + | − | + |
| FUNGI |  |  | Nystatin (100 u/disc) |
| *Aspergillus* spp. | + | − | + |
| *Penicillium* spp. | + | − | + |

Application of the Invention

The product of the invention is effective on *Escherichia coli*, *Pseudomonas aeruginosa*, MRSA, and *Staphylococcus aureus* bacteria; yeast, *Candida* spp.; and fungal species, *Aspergillus* spp. and *Penicillium* spp.

In the hydrophobic non-woven samples on which the invention is applied, the solution of alkyl polyglycoside (glucopon)+triclosan+chlorhexidin+disodium octaborate pentahydrate+distilled water ((dH2O) enables the antimicrobial mixture to be coded into the textile products by allowing the hydrophobic surface to be transformed to a hydrophilic surface.

These textile products can be used in;

medical sector: for dialysis filters, band-aids, surgical gowns, masks, caps, surgical threads, and drapes, garment sector: parts of the cloths such as stiffening cloth and interlining in work uniforms requiring hygiene, underwear and summer cloths such as shorts, bikinis and bathing suits which are very much exposed to moisture and provide a suitable setting for reproduction of bacteria, and baby clothing requiring hygiene, home and workplace textile: carpets, curtains, furnishings, table cloths, bedspreads, head rest covers, and other textile products that require hygiene in public transportation vehicles, all textile products that may be used for packaging, storing and transporting foodstuff, façade linings and insulations in construction sector; in areas where microorganisms can be prevented from proliferating and causing rotting.

The invention claimed is:

1. A method comprising the steps of:
dissolving triclosan in an alkyl polyglycoside and obtaining a homogenous mixture,
adding chlorhexidine solution to the homogenous mixture to obtain a solution mixture,
adding disodium octaborate pentahydrate to the solution mixture to form a homogenous impregnation solution,
loading the homogenous impregnation solution on textile products thereby making the textile products antimicrobial,
passing the textile products through at least one roller thereby recovering an excess solution,
drying the textile products, which are loaded with the impregnation solution, by passing them through at least one oven,
obtaining a final antimicrobial textile product.

2. The method according to claim 1, wherein triclosan is dissolved in 10% alkyl polyglycoside at a concentration of 0.001-0.1% at 45° C. and a homogenous mixture is obtained.

3. The method according to claim 1, wherein 20% chlorhexidine solution is added to the homogenous mixture at a concentration of 0.05-3%.

4. The method according to claim 1, wherein disodium octaborate pentahydrate is added to the solution at a concentration of 0.001-0.1% for the homogenous impregnation solution.

5. The method according to claim 1, wherein the step of drying the textile products, which are loaded with the impregnation solution, by passing them through at least one oven is performed by passing the products through an oven at 60° C. at a speed of 12 meters/minute.

6. The method according to claim 1, wherein the homogenous impregnation solution transforms a plurality of hydrophobic textile surfaces to a plurality of hydrophilic surfaces and codes antimicrobial property to the textile surfaces.

7. A plurality of antimicrobial textile products obtained with the method according to claim 1.

8. The textile products according to claim 7 which have antimicrobial activity against bacteria, yeasts and fungi.

9. The textile products according to claim 8, which are effective against bacterial species of *Escherichia coli, Pseudomonas aeruginosa*, MRSA, and *Staphylococcus aureus*.

10. The textile products according to claim 8, which are effective against yeast, *Candida* spp.

11. The textile products according to claim 8, which are effective against fungal species of *Aspergillus* spp and *Penicillium* spp.

\* \* \* \* \*